United States Patent [19]

Orlowski et al.

[11] Patent Number: 4,479,782

[45] Date of Patent: Oct. 30, 1984

[54] VISIBLE LIGHT-CURED ORTHODONTIC ADHESIVE

[75] Inventors: Jan A. Orlowski, Altadena; David V. Butler, West Covina, both of Calif.

[73] Assignee: Scientific Pharmaceuticals, Inc., Duart, Calif.

[21] Appl. No.: 485,889

[22] Filed: Apr. 18, 1983

[51] Int. Cl.$^3$ ............................................... A61K 5/06
[52] U.S. Cl. ................................. 433/220; 523/116; 433/9
[58] Field of Search ............... 433/9, 220; 260/998.11; 204/159.23; 523/116

[56] References Cited

U.S. PATENT DOCUMENTS

| | | | |
|---|---|---|---|
| 3,194,783 | 7/1965 | Bowen | 260/41 |
| 3,541,068 | 11/1970 | Taylor | 260/41 R |
| 3,597,389 | 8/1971 | Taylor | 260/41 R |
| 3,629,187 | 12/1971 | Waller | 260/41 R |
| 3,721,644 | 3/1973 | Stoffey et al. | 260/41 A |
| 3,730,947 | 5/1973 | Stoffey et al. | 526/232 |
| 3,751,399 | 8/1973 | Lee et al. | 526/309 |
| 3,774,305 | 11/1973 | Stoffey et al. | 32/15 |
| 3,834,932 | 9/1974 | Brandl | 156/60 |
| 3,860,556 | 1/1975 | Taylor | 260/998.11 |
| 4,107,845 | 8/1978 | Lee et al. | 260/998.11 |
| 4,304,893 | 12/1981 | Orlowski | 204/159.23 |
| 4,340,529 | 7/1982 | Lee et al. | 433/9 |
| 4,407,984 | 10/1983 | Ratcliffe et al. | 433/228 |
| 4,411,625 | 10/1983 | Koblitz et al. | 433/222 |

*Primary Examiner*—Veronica P. Hoke
*Attorney, Agent, or Firm*—Cushman, Darby & Cushman

[57] ABSTRACT

There is provided a method of bonding orthondontic brackets to teeth with an adhesive comprised of a mixture of an aromatic or hydroaromatic and aliphatic methacrylate or acrylate, an alpha, $\beta$-diketone and a tertiary amine and, optionally, organic or inorganic fillers, polymerization stabilizers and other additives, such adhesive being cured by a light source having white-light output of no less than 25,000 foot candles. The light is applied to the occlusal surface of the tooth or the side opposite to the side on which the bracket is placed. Thus the adhesive is irradiated indirectly.

25 Claims, No Drawings

VISIBLE LIGHT-CURED ORTHODONTIC ADHESIVE

FIELD OF THE INVENTION

This invention concerns a method of bonding orthodontic brackets to human teeth using an acrylic resin-based adhesive containing an alpha-beta diketone and a tertiary amine as the polymerization initiating system and a light source having the white-light output of at least 25,000 foot candles in the wave-length range of 380 to 500 mm. The adhesive is irradiated indirectly through the tooth structure by applying the light to the occlusal surface of the tooth for occlusal surfaces of the teeth or to the side opposite to the side on which the bracket is placed (lingual or buccal). When plastic brackets or metal brackets with perforated based are used, the adhesive may be irradiated directly through the bracket base.

BACKGROUND OF THE INVENTION

The direct bonding technique represents a relatively new development in orthodontics. It Offers several advantages over the older banding technique, which includes, among others, improved esthetics, greater patient comfort, reduction in the incidence of tooth decalcification, elimination, in some cases, of the necessity of extracting teeth, chair-time savings and facilitation of the bonding to partially erupted teeth. The adhesives used for bonding orthodontic brackets, plastic or metal, to human teeth differ in their form and application techniques. The direct bonding adhesives which are currently being used, belong to one of the following categories.
1. A four-component system comprised of two liquids which cure when mixed together and are applied on acid etched teeth as a primer and two pastes which cure when mixed together and are applied over the primer to bond the bracket.
2. A simplified system comprised of only two pastes which cure upon mixing; such a paste being of a lighter consistency than the paste described in Point 1 and therefore, not requiring priming.
3. A powder and liquid system which cures upon mixing together. Usually such a mix is thin enough to allow for the elimination of the use of the primer.
4. A two-component system representing two light-consistency pastes or a liquid and a paste; one of such components is applied to the tooth and the other on the bracket. Such a system cures when the bracket is pressed against the tooth and, therefore, both components come into contact.
5. A UV-cured system comprises of one or two components (a liquid primer and a paste or a light-consistency paste only) which cures upon exposure to light with a wave-length of 300-400 nm. Such a system is suitable for use with transparent plastic brackets or with metal brackets having perforated bases only.

The first four types described above belong to the self-curing category and they share common disadvantages such as limited working time, limited shelf-life, difficulties in cleaning off the excess material around the bracket periphery and susceptibility to operator error in mixing proportions, misjudegment of working time, etc. which may result in adhesive failures. The UV-cured adhesives suffered severe limitations as their use was limited to the type of brackets that are inadequate in the majority of applications (plastic brackets) or to the brackets of an obsolete style and inferior in performance (metal brackets with perforated bases).

While the adhesives of the prior art are used with success, their limitations and shortcomings are well recognized. There is a recognized need for an one-component adhesive which is thermally-stable and universal in application when it comes to the design of the bracket used, clinical situations and adaptability to various techniques. Such adhesive should cure only after it is activated and should reach its maximum strength in a very short time. Therefore, such an adhesive would allow the operator to correct the bracket position whenever and wherever desirable, to bond to either the buccal or lingual tooth surfaces, to easily remove excess material and also would allow for substantial chair-time savings.

SUMMARY OF THE INVENTION

This invention is directed to the method of bonding orthodontic brackets to human teeth comprised of the application of the adhesive consisting essentially of the mixture of (1) aromatic or hydroaromatic and (2) aliphatic acrylate or methacrylate and a minor amount of an alpha-beta diketone and a tertiary aromatic amine as polymerization initiators. Optionally, such an adhesive may also contain thickening agents and/or fillers, stabilizers, UV absorbers, fluorescent agents and other additives. The adhesive is applied on the properly prepared tooth surface, which normally involves acid etching, or on the bracket base. The bracket is placed on the tooth and positioned as desired and excess material is removed. The adhesive is, thereafter, cured by irradiation with a light source having a white-light output in the 380–500 nm range of at least 25,000 but preferably over 50,000 foot candles. When the metal brackets with solid (non-perforated) bases are used, the light should be applied on the side opposite to the side on which the bracket is placed (i.e., to the lingual side for buccal appliances and to the buccal side for lingual appliances) or to the occlusal surface of the tooth. When transparent plastic brackets are used or when metal brackets with perforated bases are used, the adhesive may also be cured by irradiating the side of the tooth on which the bracket is placed.

Thus there is used a combination of a highly reactive adhesive system, a visible light source having adequate intensity and a method of applying such a light to the opposite side of the tooth in respect to the side on which the bracket is placed, or to the occlusal surface of the tooth. This technique offers substantial time-savings for the operator, greater reliability and applicability in certain clinical situations in which the prior art self-cured adhesives were inadequate.

The examples of the aromatic or hydroaromatic acrylates or methacrylates which may be used according to the invention are represented by, but not limited to, diglycidylether of bisphenol A dimethacrylate (Bis-GMA) and its carbamate derivatives, e.g. with N-butyl isocyanate, ethoxylated bisphenol A dimethacrylate, bisphenol A dimethacrylate, 1,4 bis(3-methacroyl-2-hydroxypropyl)methyl)cyclohexane and its carbamate derivatives, e.g. with 4,4'-diisocyanato-dicyclohexyl methane, tris-(methacroyl-2-hydroxypropyl)trimellitate and its carbamate derivatives, e.g. with hexamethylene diisocyanate.

Likewise, there can be employed the diglycidylether of bisphenol A diacrylate, ethoxylated bisphenol A diacrylate, 1,4 bis(3-acroyl-2-hydroxypropyl methyl)-cyclohexane, acryloyl-2-hydroxypropyl trimellitate.

There can be used any of the aromatic or hydroaromatic acrylates or methacrylates disclosed in Orlowski U.S. Pat. No. 4,304,893, Waller U.S. Pat. No. 3,629,187, Stoffey U.S. Pat. No. 3,774,305, Lee U.S. Pat. No. 4,107,845, Bowen U.S. Pat. No. 3,194,783, Taylor U.S. Pat. No. 3,541,068, Taylor U.S. Pat. No. 3,597,389, Stoffey U.S. Pat. No. 3,730,947, Lee U.S. Pat. No. 3,751,399, Taylor U.S. Pat. No. 3,860,556 and Stoffey U.S. Pat. No. 3,721,644. The entire disclosures of each of the above-identified U.S. patents are hereby incorporated by reference and relied upon.

To make the mono or dicarbamate the free hydroxy groups (or epoxy groups) of the acrylate or methacrylate can be reacted with a monoisocyanate of the formula $R_1$—N=C=O where $R_1$ is an aliphatic, aromatic or cycloaliphatic group having 1 to 14 carbon atoms, e.g. a hydrocarbon group such as alkyl, aryl, aralkyl, or cycloalkyl or a haloaryl group such as chloroaryl. Examples of groups represented by R1 include methyl, ethyl, propyl, n-butyl, isobutyl, sioamyl, n-amyl, hexyl, n-octyl, isooctyl, decyl, dodecyl, tetradecyl, phenyl, p-ethyl phenyl, benzyl, p-tolyl, o-tolyl, p-butylphenyl, xylyl, α-naphthyl, p-ethyl benzyl, p-chlorophenyl, cyclopentyl, m-chlorophenyl and cyclohexyl. A preferred group for $R_1$ is n-butyl. Likewise the dicarbamates can be prepared by reacting hydroxy or epoxy group containing diacrylates or dimethacrylates with a diisocyanate of the formula O=C=N—$R_2$—N=C=O where $R_2$ is an aliphatic, cycloaliphatic or aromatic group having 6 to 15 carbon atoms. Examples of such diisocyanates include hexamethylene diisocyanate, octamethylene diisocyanate, decamethylene diisocyanate, undecamethylene diisocyanate, dodecamethylene diisocyanate, xylene-1,4-diisocyanate, xylene-1,3-diisocyanate, m-phenylene diisocyanate, durylene diisocyanate, benzidene diisocyanate, 1-methyl phenylene-2,4-diisocyanate, naphthlene-1,4-diisocyanate, naphthylene-1,5-diisocyanate, 3,3'-dimethyl-4,4'-diisocyanato diphenyl methane, 4,4'-diphenyl propane diisocyanate, dianisidine diisocyanate, cyclohexamethylene-1,4-diisocyanate, cyclohexamethylene-1,3-diisocyanate and 4,4'-diisocyanate dicyclohexyl methane. Preferred diisocyanates include hexamethylene diisocyanate and 4,4'-diisocyanato dicyclohexyl methane.

Additional examples of mono and diisocyanates which can be employed are set forth in the above-mentioned (and relied upon) Waller U.S. Pat. No. 3,629,187.

The hydroaromatic or aromatic acrylate or methacrylate should have at least two ethylenically unsaturated double bonds.

Various aliphatic mono and diacrylates or dimethyl higher polyacrylates or methacrylates are suitable for use in the formulation according to the invention, however, the use of the following were found to be especially advantageous. $C_1$-$C_4$ alkyl methacrylates, $C_1$-$C_2$ alkoxyalkylmethacrylates, $C_1$-$C_{10}$ alkylene dimethacrylates, ethylene and polyethylene glycol dimethacrylates and diacrylates, pentaerythritol tetramethacrylates or acrylate and trimethylolopropanetrimethacrylates or triacrylate.

Illustrative acrylates and methacrylates include methyl acrylate, methyl methacrylate, ethyl acrylate, ethyl methacrylate, butyl acrylate, butyl methacrylate, ethylene diacrylate, ethylene dimethacrylate, propylene diacrylate, propylene dimethacrylate, trimethylene dimethacrylate, tetramethylene diacrylate, tetramethylene dimethacrylate, hexamethylene diacrylate, hexamethylene dimethacrylate, decamethylene diacrylate, decamethylene dimethacrylate, diethylene glycol diacrylate, diethylene glycol dimethacrylate, triethylene glycol dimethacrylate, tetraethylene glycol diacrylate, tetraethylene glycol dimethacrylate, pentaerythritol tetracrylate and trimethylolpropane triacrylate.

Preferably the aliphatic acrylate or methacrylate has at least two ethylenic double bonds. As alpha-beta diketone, the camphoroquinone, 2,3-bornanedione, and benzil are preferred. The tertiary amines include, but are not limited to, methacroyl (or acroyl) alkyl-dialkyl or dihydroxyalkyl amines and trialkylamines, having, preferably, one to ten carbon atoms in the alkyl moieties. Examples of such amines are tributylamine, tripropylamine, tridecylamine, butyl diethanoloamine, methyl, ethyl, propyl or butyl diethanoloamine, butyl dimethylamine, methacroylethyldimethylamine, methacroylethyl-diethylamine, cyclohexyl diethanoloamine. There can be used tertiary aromatic amines, e.g. N,N-dimethyl-p-toluidine or N,N-bis(2-hydroxyethyl)-p-toluidine or any of the tertiary aromatic amines set forth in the above-mentioned patents. Preferably the tertiary amine has at least one ethylenically unsaturated group and is most preferably an aliphatic amine having such an unsaturated group. The unsaturated group enables the tertiary amine to copolymerize with the acrylate or methacrylate. Illustrative fillers are also shown in the aforementioned U.S. patents, e.g. the Orlowski U.S. Pat. No. 4,304,893. As fillers, inorganic and organic materials may be used. As organic fillers, various polymeric materials were found to be suitable, particularly the polymers of methacrylate esters including cross-linked polymethyl and polyethylmethacrylates and polymerized aliphatic dimethacrylates, e.g. polymerized ethylene dimethacrylate. As inorganic fillers, various natural and synthetic silicas, quartz and glasses may be used. As additives, the use of commonly applied polymerization stabilizers such as BHT (butylated hydroxy toluene), hydroquinone, methylhydroquinone and materials of similar function were found to be suitable.

The preferred formulation of the adhesive should contain, in its resin portion, no less than 40% but preferably 50 to 80% of aromatic or hydroaromatic methacrylates of corresponding acrylates. The resin can contain 10 to 50% or even 60% or even 73% of the aliphatic acrylate or methacrylate but as indicated preferably 20 to 50% of the resin portion comes from the aliphatic acrylate or methacrylate. An illustrative range of aromatic or hydroaromatic to aliphatic methacrylate or acrylate is 0.4:1 to 4:1 by weight.

The concentratin of alpha-beta diketones should be no less than 0.1% but preferably is 0.2 to 1%. The concentration of the amine should be no less than 0.1% but preferably is no less than 0.4% per weight of the resin portion of the adhesive and can be as much as 10%. The use of the filler or other thickening agent is not critical but may be desirable to optimize the consistency of the adhesive and its handling properties. Usually the filler (when employed) is used in a concentration of 5 to 85% per the weight of the adhesive.

Various commercially available light sources are suitable to be used in the procedure according to the invention. Examples of such light sources are:

1. Initiator (the product of Solid State Systems, Inc.).
2. Sunlite (the product of Kinetic Instruments, Inc.).
3. Optilux (the product of Demetron Research Corp.).

4. Other light sources having an output in the range of 380–500 mm of at least 25,000 foot candles but preferably over 50,000 foot candles are suitable.

The instruments should emit light from a narrow tip, e.g. of about 0.8 cm in diameter and the light's design should permit the easy manipulation of such a tip that would allow for proper positioning of the light in the patient's mouth. The irradiation time depends on the intensity of the light and on the clinical situation, i.e., on the size, geometry and color of the tooth, presence of the restorations, etc. Typically, the anterior teeth are irradiated from the side opposite the side on which the bracket is placed. Thus, when the brackets are positioned on the buccal side of the tooth, the tip of the light should be positioned on the lingual side of the tooth. For lingually placed applicances, the light tip should be positioned on the buccal side of the tooth. For posterior teeth, that are characterized by a greater thickness, it is advantageous or sometimes necessary, to position the light tip on the occlusal surface of the tooth. Curing of the adhesive through the bracket bases is possible only with plastic brackets and with brackets having perforated bases.

Usually, 30 to 60 seconds curing time is adequate to provide good cure. For example, the Optilux light by Demetron gave bonding strength in excess of 1,000 psi on anterior teeth after 40 seconds cure and about the same adhesive strength on posterior teeth after 50 seconds cure.

While this invention offers most desirable and long awaited improvements in orthodontic procedures, its development is the result of unexpected findings that certain formulations of the acrylic-type resins may be cured using visible light emitting instruments even when access of the light to such adhesives is only available through the tooth structure. The instruments with a light output capacity in excess of 50,000 foot candles were found to generate, at the tip, clinically acceptable amounts of heat while providing enough light intensity to cure the adhesive through the tooth structure. Wherever the thickness of the tooth or its color caused the quality of cure obtainable, when the light was positioned on the opposite side of the bracket, to be inadequate, or the curing time required was excessively long, it was found, surprisingly, that good cure may be obtained by positioning the tip of the light of the occlusal surface. Such positioning of the light tip was especially advantageous on posterior teeth. The method of attaching orthodontic brackets to the tooth structure, according to the invention, was found, surprisingly, reliable and reproducible on anterior and posterior teeth, with plastic and metal brackets, regardless of the design of the bracket bases. In addition to the conveniences and advantages resulting from controlling the curing procedure, the technique according to the invention offers substantial time savings. The full strength of the adhesive is obtainable virtually immediately after the completion of irradiation, i.e., within 60 seconds while self-cured adhesives normally require about two minutes curing time followed by at least a five-minutes post-curing period, during which the adhesive gains strength. The combination of the chemical make-up of the adhesive of this invention with the technique of irradiation brought a surprising result that was unforeseeable on the basis of the prior art.

The process can comprise, consist essentially of, or consist of the stated steps with the recited materials. Likewise the compositions can comprise, consist essentially of, or consist of the recited materials.

This invention will be better understood by reference to the examples given below which should not be interpreted, however, as limiting its scope. Unless otherwise indicated all parts and percentages are by weight.

EXAMPLE 1

An extracted maxiliary central tooth having a shade conforming to the Bioform Shade Guide #65 was etched with 33% phosphoric acid for two minutes, washed and dried. The adhesive, whose formulation is given below, was applied in a thin layer to the bracket base and the bracket positioned on the buccal surface of the tooth (medium-twin Ormco metal bracket was used). The tooth was irradiated for 40 seconds with Demetron's Optilux light with the tip of the light being applied against the lingual side of the tooth. The bonding strength was tested by applying force parallelly to the long axis of the tooth. The bracket did not separate from the tooth under a shear load of 50 pounds.

Composition of the adhesive:
Diglycidyl ethyl of bisphenol A dimethacrylate: 70
Hexanedioldimethacrylate: 30
Camphoroquinone: 0.3
Methacroylethyldimethylamine: 0.8
Fumed Silica: 17

EXAMPLE 2

The medium-twin bracket as described in Example 1 was bonded to the buccal surface of an etched molar tooth having the color corresponding to the Bioform Shade Guide No. 68. The light was applied to the occlusal surface of the tooth for 60 seconds. The force needed for separation of the bracket from the tooth was in excess of 50 pounds. The formulation of the adhesive is given below:

Composition of the adhesive:
Diglycidyl ether of bisphenol A dimethacrylate: 20
Di-N-butyl carbamate of bisphenol A dimethacrylate: 40
Triethylene glycol dimethacrylate: 40
Camphoroquinone: 0.25
Benzil: 0.2
Diethanoloaminobutylamine: 0.4
Methacroylethyldiethylamine: 0.4
Hydrophobized quartz (100% below 5 microns): 200
Amphorous Silica: 7

EXAMPLE 3

The adhesive described in Example 1 was used for bonding plastic brackets manufactured by Tella-Tech Inc.; size: wide. Prior to the application of the adhesive, the bracket base was primed with a mixture of 70% methylmethacrylate and 30% Bis-GMA. The bracket was placed on the buccal side of a maxiliary central tooth having the color corresponding to Bioform Shade Guide No. 59. The tip of the light was positioned directly against the bracket for an irradiation time of 60 seconds. It was found that the bonding strength, under shear forces, was in excess of 40 pounds (under which load the bracket deformed).

What is claimed is:

1. A method of bonding an orthodontic bracket to a human tooth with a visible light-activated adhesive comprised of a mixture of (1) an aromatic or hydroaromatic acrylate or methacrylate having at least two ethylenic double bonds with (2) an aliphatic acrylate or methacrylate, (3) an alpha, beta diketone and (4) a tertiary amine comprising curing said adhesive by irradiation with a light source having a white-light output in the range of 380–500 nanometers of at least 25,000 foot candles, such light being applied to the occlusal surface of the tooth or to the side opposite to the side on which the bracket is placed.

2. A method according to claim 1 wherein the adhesive is indirectly irradiated by light from said light source.

3. A method according to claim 2 wherein the light is applied to the occlusal surface of the tooth.

4. A method according to claim 2 wherein the light is applied to the side of the tooth opposite to the side on which the bracket is placed.

5. A method according to claim 2 wherein the aromatic or hydroaromatic acrylate or methacrylate is 90 to 27% of the total weight of (1) and (2) and the aliphatic acrylate or methacrylate is 10 to 73% of the total (1) and (2).

6. A method according to claim 5 wherein the aromatic or hydroaromatic acrylate or methacrylate is 90 to 40% of the total of (1) and (2).

7. A method according to claim 6 wherein the aromatic or hydroaromatic acrylate or methacrylate is 80 to 50% of the total of (1) and (2).

8. A method according to claim 5 wherein the weight ratio of the aromatic or hydroaromatic acrylate or methacrylate (1) to the aliphatic acrylate or methacrylate (2) is 0.4:1 to 4:1.

9. A method according to claim 2 wherein the aliphatic acrylate or methacrylate has at least two ethylenic double bonds.

10. A method according to claim 8 wherein the aliphatic acrylate or methacrylate has at least two ethylenic double bond.

11. A method according to claim 9 wherein the tertiary amine has at least one polymerizable ethylenic double bond.

12. A method according to claim 8 wherein the tertiary amine has at least one polymerizable ethylenic double bond.

13. A method according to claim 9 wherein the aromatic or hydroaromatic acrylate or methacrylate comprises the diglycidyl ether of bisphenol A methacrylate.

14. A method according to claim 13 wherein the aromatic or hydroaromatic acrylate or methacrylate is the diglycidylether of bisphenol A methacrylate alone or admixed with the di-N-butyl carbamate of bisphenol A dimethacrylate.

15. A method according to claim 14 wherein the tertiary amine comprises methacroylethyldimethylamine or methacroylethyldiethylamine.

16. A method according to claim 15 wherein the concentratin of the alpha, beta diketone is 0.1–2 parts per 100 parts of total acrylate or methacrylate.

17. A method according to claim 2 wherein the concentration of the alpha, beta diketone is 0.1–2 parts per 100 parts of total acrylate or methacrylate.

18. A method according to claim 17 in which the alpha, beta diketone comprises camphoroquinone or benzil.

19. A method according to claim 17 wherein the concentration of tertiary amines is 0.2–10 parts per 100 parts of the total acrylate or methacrylate.

20. A method according to claim 18 wherein the concentration of tertiary amines is 0.2–10 parts per 100 parts of the total acrylate or methacrylate.

21. A method according to claim 20 wherein the tertiary amine comprises methacroylethyldimethylamine, methacroylethyldiethylamine, tributylamine, tripropylamine, methyldiethanoloamine, propyldiethanoloamine, or butyldiethanoloamie.

22. A method according to claim 2 wherein the adhesive contains a mineral or organic filler, the filler being present in an amount of up to 85%.

23. A method according to claim 2 wherein the light source has an output in the range of 50,000 to 120,000 foot candles.

24. A method according to claim 23 wherein the irradiation time for bonding a bracket is 20–300 seconds.

25. A method according to claim 2 wherein the irradiation time for bonding a bracket is 20–300 seconds.

* * * * *